(12) United States Patent
Okubo et al.

(10) Patent No.: US 7,502,648 B2
(45) Date of Patent: Mar. 10, 2009

(54) ARTIFICIAL CARDIAC PUMP

(75) Inventors: Takeshi Okubo, Takasago (JP);
Toshiyuki Osada, Takasago (JP);
Yasuharu Yamamoto, Takasago (JP);
Takeshi Sano, Takasago (JP); Yusuke Miyamoto, Takasago (JP); Kazuyoshi Miyagawa, Takasago (JP)

(73) Assignee: Mitsubishi Heavy Industries, Ltd., Tokyo (JP)

(*) Notice: Subject to any disclaimer, the term of this patent is extended or adjusted under 35 U.S.C. 154(b) by 0 days.

(21) Appl. No.: 10/552,418

(22) PCT Filed: Apr. 23, 2004

(86) PCT No.: PCT/JP2004/005888

§ 371 (c)(1),
(2), (4) Date: Feb. 1, 2006

(87) PCT Pub. No.: WO2004/096320

PCT Pub. Date: Nov. 11, 2004

(65) Prior Publication Data

US 2006/0183962 A1 Aug. 17, 2006

(30) Foreign Application Priority Data

Apr. 30, 2003 (JP) ............................. 2003-124645
Mar. 11, 2004 (JP) ............................. 2004-068451

(51) Int. Cl.
*A61M 1/10* (2006.01)
(52) U.S. Cl. ...................................................... 607/16
(58) Field of Classification Search .................. 600/16;
623/3.1, 3.13; 604/264
See application file for complete search history.

(56) References Cited

U.S. PATENT DOCUMENTS 3,143,972 A 8/1964 Smith et al.
5,112,200 A 5/1992 Isaacson et al.

(Continued)

FOREIGN PATENT DOCUMENTS

EP 1 114 648 A2 7/2001

(Continued)

*Primary Examiner*—Carl H Layno
*Assistant Examiner*—Brian T Gedeon
(74) *Attorney, Agent, or Firm*—Wenderoth, Lind & Ponack, L.L.P.

(57) ABSTRACT

An artificial cardiac pump includes an impeller (3) rotatably supported on a fixed shaft body (2) in a housing (1) and a drive mechanism rotating the impeller, wherein blood is taken in from the front side and force-fed to the rear side by the rotation of the impeller (3). The shaft body (2) is connected between a front side fixed body (5) fixed to a straightening plate (4) joined to the housing (1) at the front of the impeller (3) and a rear side fixed body (7) fixed to a diffuser (6) joined to the housing (1) at the rear of the impeller (3). The impeller (3) further includes a sleeve (8) having an inner peripheral surface opposed to the outer peripheral surface of the shaft body (2) through a minute clearance and front and rear end faces opposed to the rear end face of the front side fixed body (5) and the front end face of the rear side fixed body (7) through minute clearances, and an impeller (9) joined to the outer peripheral surface of the sleeve (8). The drive mechanism further includes a polar anisotropical permanent magnet (10) enclosed in the sleeve (8) and a rotating field generator (11) enclosed in the housing (1).

6 Claims, 4 Drawing Sheets

U.S. PATENT DOCUMENTS

| | | | |
|---|---|---|---|
| 5,211,546 A * | 5/1993 | Isaacson et al. | 417/356 |
| 6,015,272 A * | 1/2000 | Antaki et al. | 417/356 |
| 6,244,835 B1 | 6/2001 | Antaki et al. | |
| 6,368,075 B1 * | 4/2002 | Fremerey | 417/365 |
| 6,447,265 B1 | 9/2002 | Antaki et al. | |
| 2001/0031210 A1 | 10/2001 | Antaki et al. | |

FOREIGN PATENT DOCUMENTS

| | | |
|---|---|---|
| JP | 7-189972 | 7/1995 |
| JP | 11-13682 | 1/1999 |
| JP | 2000-502420 | 2/2000 |
| JP | 2002-130177 | 5/2002 |
| JP | 2003-503639 | 1/2003 |
| WO | 97/49440 | 12/1997 |
| WO | 98/11650 | 3/1998 |
| WO | 00/64030 | 10/2000 |
| WO | 01/02724 | 1/2001 |

* cited by examiner

ARTIFICIAL CARDIAC PUMP

FIELD OF THE INVENTION

The present invention relates to an artificial cardiac pump for force-feeding blood as a substitute or an auxiliary of a heart of a living body.

BACKGROUND OF THE INVENTION

In the conventional art, an artificial cardiac pump comprises a rotatable impeller so as to be taken and force-fed blood. In general, artificial cardiac pumps can be divided into a group of axial-flow propeller pumps and a group of rotary/centrifugal pumps. Upon comparing the group of the axial-flow propeller pumps with the group of rotary/centrifugal pumps, the group of the axial-flow propeller pumps has an advantage in view of down-sizing. Hereinafter, an artificial cardiac pump with an axial-flow propeller pump will be described.

For example, a conventional artificial cardiac pump comprises a rotor such as an impeller, wherein both ends of the rotor are rotatably supported in a housing and a polar anisotropic permanent magnet is installed in the rotor, and a motor stator such as a rotary magnetic flux generator, wherein the motor stator surrounds with a peripheral of the rotor and is installed in the housing. By magnetic co-relation between the polar anisotropic permanent magnet and the motor stator, the rotor can be rotated with respect to the housing. Under such a structure, a characteristic of an artificial cardiac pump having a typically axial flow propeller pump can be obtained. That is, blood is taken from the front side and force-fed to the rear side by rotating the impeller.

In the above conventional art, a rotor comprises a rotational axial member of which both sides are supported, and impeller wing-components protruded from an outer peripheral surface of the rotational axial member [i.e. Japanese Patent Publication 2001-523983 (pages 23-26, FIGS. 4 and 9)]. Another rotor further comprises a shroud adjoined at an outer peripheral surface of the impeller and coaxially located with respect to the rotational axial member [i.e. U.S. Pat. No. 6,053,705]. In the former case, a polar anisotropic permanent magnet is installed in the rotational axial member. In the latter case, a polar anisotropic permanent magnet is installed in the shroud. In the former case of the artificial cardiac pump, the shroud is unnecessary and a structure thereof can be simplified. Therefore, it is advantageous in view of down-sizing. On the other hand, in the latter case of the artificial cardiac pump, the anisotropic permanent magnet and the motor stator can be alternatively and closely arranged. Therefore, it is advantageous in view of a motor driving effort for rotating a rotor.

However, in the above described conventional artificial cardiac pumps, both sides of the rotor are supported by fixed receiving parts of the housing in a contact relation. Thus, both sides are worn down and burned, such that mechanical loss and damages occur. In addition, blood is apt to be adhered/condensed around abraded powder as a core. Finally, a blood flowing route such as a blood vessel becomes narrower and a thrombus would occur.

Concerning such problems, the inventors provide an artificial cardiac pump having a housing in which a rotor is rotatably supported in a non-contact relation. An improved artificial cardiac pump provided by the inventors will be described with reference to FIG. 3.

Figure 3:
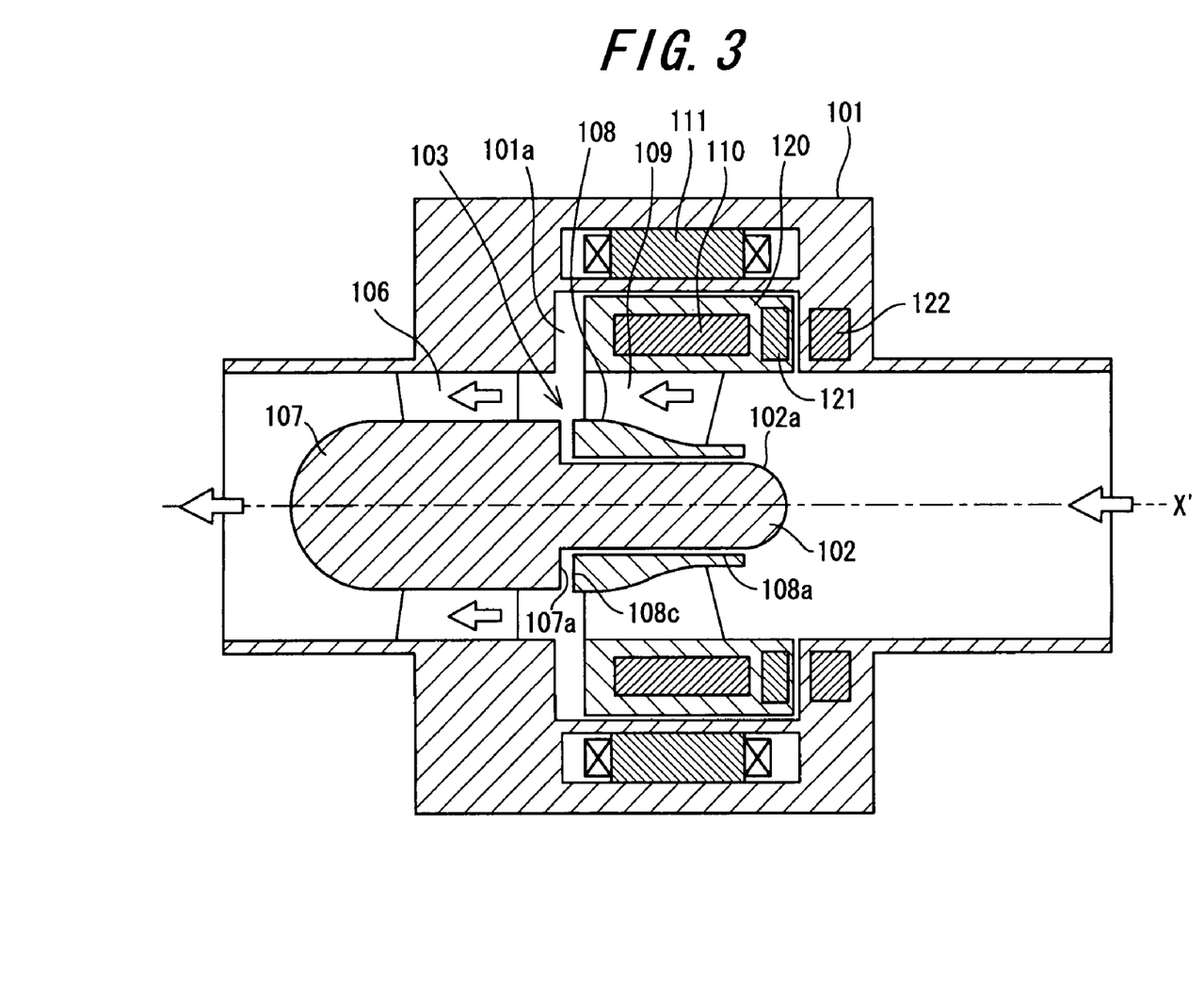
FIG. 3 shows a vertical cross sectional view of a conventional improved artificial cardiac pump.

As shown in FIG. 3, the improved artificial cardiac pump comprises a cylindrical housing 101, a rotor 103 rotatively supported in the housing 101 in a non-contact relation, a plurality of board-shaped diffuser components 106 protruded from an inner wall of the housing 101 at a rear side with respect to the rotor 103, a rear side fixing body 107 connected with an inner side edge of the diffuser 106 and an axial body 102 fixed on a front end surface 107a of the rear side fixing body 107. Thereby, a fixed axial body 102 is coaxially arranged with respect to a central axis X' in the housing 101.

The axial body 102 has an outer peripheral surface 102a on which an inner peripheral surface 108a of a sleeve 108 is circularly fitted. The sleeve 108 is rotatably and movably supported with respect to the axial body 102 along an axial direction. A plurality of impeller wing-components 109 are protruded from and fitted on an outer peripheral surface of the sleeve 108. Further, at an outer edge of the impeller, a cylindrical shroud 120 is coaxially fitted with respect to the sleeve 108. The housing 101 includes a circular shroud receiving groove 101a into which the shroud 120 is installed. An inner wall of the circular shroud receiving groove 101 closely confronts with an outer peripheral surface of the shroud 120. The rotor 103 is formed by the sleeve 108, the impeller 109 and the shroud 120.

Inside of the shroud 120, polar anisotropic permanent magnets 110 are radially arranged with respect to the central axis X'. At a front side thereof, a ring-shaped shroud 120 is installed in the shroud 120. The polar anisotropic permanent magnets produce magnet flux perpendicular to the outer peripheral surface of the shroud 120. The permanent magnet 110 produces magnetic flux parallel to the outer peripheral surface of the shroud 120. On the other hand, in the housing 101a motor stator 111 is arranged at a peripheral portion of a shroud receiving grooved portion 101a in order to surround the shroud 120, wherein the motor stator 111 comprises an electromagnetic coil for producing magnetic flux towards the outer peripheral surface of the shroud 120. In front of the shroud receiving groove portion 101 in the housing, a ring-shaped permanent magnet 122 is installed so as to produce magnetic flux perpendicular to the front end surface of the shroud 120.

In accordance with such an improved artificial cardiac pump, rotational force is transmitted to the polar anisotropic permanent magnets 110 of the motor stator 111 by conducting electric current having different phases such as three phase electric current in an electromagnetic coil. Thus, the sleeve 108, the impeller 109 and the shroud 120 of the rotor are integrally rotated around the fixed axial body 102 in the housing 101. Thereby, blood is sucked from the front side and taken into the housing 101. The blood is pressurized by the impeller 109 and flown into the diffuser 106. A hydrodynamic status is recovered to a static status, while the blood is discharged to a rear side. In FIG. 3, a blood flowing route is shown as white arrows.

A blood pressure level at a rear side (downstream) with respect to the impeller 109 is higher than that at a front side thereof (upstream). Under the above structural condition, a load is applied on the rotor itself along a direction from the rear side to the front side. As the result, the front end surface of the shroud 120 is moved towards a front end surface of the shroud receiving groove portion 101a in the housing. However, a repulsion force between the permanent magnets 121 and the permanent magnet 122 is produced since the same magnetic poles face each other. Thus, a contact/collision between the shroud 120 and the housing 101 can be prevented. A portion of the high pressurized blood in the rear side portion of the impellers 109 is flown to an end surface of the shroud receiving groove portion 101a of the housing 101, a rear side surface of the shroud 120, an outer peripheral surface of the shroud 120 and a gap between the front end surface and the housing 101 in order by utilizing a blood pressure difference. Thus, the blood stream is joined with blood at the front side portion of the impellers 109, that is, the blood taken into the housing 101.

The blood pressure difference as described above is utilized to support the rotor 103. That is, the sleeve 108 is supported with respect to the axial body 102 in a non-contact relation. The portion of the high pressurized blood at the rear side portion of the impeller 109 is introduced to a micro gap between an outer peripheral surface 102a of the axial body 102 and an inner peripheral surface 108a of the sleeve 108 from a back side with respect to the sleeve 108 through a gap between the front end surface 107a of the rear fixed body 107 and the rear end surface 108c of the sleeve 108. Then, the blood is joined with the blood taken into the housing by forwardly force-feeding the blood through the micro gap. Accordingly, while the rotor 103 is rotating, blood is flown into the gap between the axial body 102 and the sleeve 108 as a lubricant fluid. The rotating rotor 103 is supported with respect to the axial body 102 in the non-contact relation.

As described above, in the above improved artificial cardiac pump, the rotor 102 is supported and rotated in the housing 101 in the non-contact relation so that mechanical loss (damage) and thrombus which occur in the conventional artificial cardiac pump in which a rotor is supported in a contact relation can be remarkably avoided.

However, the improved artificial cardiac pump as described above comprises a shroud 120 as one of components. Therefore, there are the following drawbacks. The shroud 120 is an outer-most wall of the rotor with respect to a radial direction. At first, unless a weight balance condition is even in the shroud 120, a dynamic balance of the rotor becomes very large in a rotational condition. The rotor cannot be rotated smoothly and such a situation is baneful for the non-contact relation and the rotor would be vibrated. The shroud 120 is the outer-most wall of the rotor with respect to the radial direction. Mechanical loss and damage caused by rotating the rotor in blood cannot be ignored. Particularly, the polar anisotropic permanent magnets 110 that rotate the rotor 103 by confronting with the motor stator 111 is installed in the rotor. Therefore, an unbalanced weight condition is apt to occur in the rotor, even if a degree of the unbalanced weight condition is small.

Second, while the rotor 103 is rotated, blood is (reversely) flown into a gap between the shroud receiving groove portion 101a and the shroud 120 in the housing so that an efficiency of the pump is restricted. If the gap between the shroud receiving grooved portion 101a and the shroud 120 becomes narrower so as to improve the efficiency of the pump, a large shearing force is applied to blood flown therein, because a peripheral rotational speed of the shroud 120 is higher than that of the shroud receiving grooved portion 101a. The large shearing force depends on a rotational speed difference between the shroud 120 and the shroud receiving grooved portion 101a. Under this situation, an outer peripheral membrane of a number of red blood corpuscles are damaged, so that a specific effect of the red blood corpuscle itself is lost and blood is dissolved.

A purpose of the present invention is to resolve the above described drawbacks. An artificial cardiac pump according to the present invention can reduce the above mechanical loss based on a structure that an impeller is supported and rotated in a housing in a non-contact relation and improve pump efficiency.

SUMMARY OF THE INVENTION

To accomplish the above purpose, an artificial cardiac pump according to the present invention comprises a housing, an impeller pivotally supported with respect to an axial body fixed in the housing and a driving mechanism for rotating the impeller, wherein blood is taken in from the front side of the impeller and force-fed to the rear side of the impeller along an axial direction by the impeller rotated by the driving mechanism, the axial body is connected and sandwiched between a front side fixed body and a rear side fixed body, wherein the front side fixed body is fixed at a straightening board protruded from an inner wall of the housing at a front side with respect to the impeller and the rear side fixed body is fixed at a board-shaped diffuser protruded from the inner wall of the housing at a rear side with respect to the impeller, the impeller comprises an inner peripheral surface confronting with an outer peripheral surface of the axial body with a micro gap, a sleeve of which the both end surfaces confronting with a rear end surface of the front side fixed body and a front end surface of the rear side fixed body with a micro gap, respectively and impeller wing-components protruded from an outer peripheral surface of the sleeve, and the driving mechanism comprises polar anisotropic permanent magnets installed in the sleeve and rotary magnetic flux generator installed in the housing and surrounding with a peripheral portion of the impeller.

Thereby, rotational force is applied to polar anisotropic permanent magnets while a rotary magnetic flux generator is driven. By rotating the impeller, blood is taken into the housing from a front side of the impeller and whirling blood is controlled through a straightening plate and pressurized to a hydrodynamic status by the impeller. The almost part of the blood is recovered to a static status by the diffusers and discharged to the rear side of the impeller. In such a case, a part of the high pressurized blood behind the impeller is introduced into a micro gap between a front end surface of a rear side fixed body and a rear end surface of a sleeve. The blood is fed to the micro gap between the rear end surface of the front fixed body and the front end surface of the sleeve through a micro gap between an outer peripheral surface of the axial body and an inner peripheral surface of the sleeve. As the result, the blood is joined with the blood fed into the housing. Accordingly, while the impeller is rotating, blood as a lubricant fluid is flown into micro gaps formed between the sleeve and the rear end fixed body, the rear end fixed body and the axial body and the axial body and the front side fixed body in order. Thus, while the impeller is rotating, radial load thereof is supported by the axial body in a non-contact relation and thrust load is supported by the rear side fixed body and the front side fixed body in a non-contact relation.

Further, the polar anisotropic permanent magnets for rotating the impeller by confronting with a rotational magnetic flux generator are surrounded with a sleeve as a component of the impeller. Therefore, the pump according to the present invention does not comprise a shroud that has to be utilized in the conventional improved artificial cardiac pump. Accordingly, even if an unbalanced weight condition occurs at the sleeve located at an innermost location of the impeller with respect to a radial direction, baneful influence against the dynamic balance for a rotating impeller is very small and the impeller does not vibrate so much. An outer diameter of the impeller can be shortened and mechanical loss and damages can be saved. In addition, reverse blood flow from the shroud that has often happened in the conventional improved artificial cardiac pump is completely resolved so that a pump efficiency can be improved.

Therein, it is preferable to provide thrust hydrodynamic generating grooves for supporting a thrust load of the impeller, wherein the thrust hydrodynamic generating grooves are provided at the rear end surface of the front side fixed body and the front end surface of the rear end fixed body, which are confronting with both end surfaces of the sleeve, respectively.

Further, while the impeller is rotating, load is applied on the impeller from a rear side to a front side due to a blood pressure gap between the front side and the rear side. Thereby, the front end surface of the sleeve approaches the rear end surface of the front side fixed body. If the front end surface of the sleeve approaches the rear end surface of the front side fixed body very closely, the micro gap cannot be sufficiently provided. Under this condition, blood as a lubricant fluid cannot be flown smoothly. If the gap becomes too narrow, mechanical loss and damages become serious and an amount of dissolved blood is increased. In order to avoid the above problems, it is preferable to install a ring-shaped magnetic body confronting with an end surface of the sleeve at the rear end fixed body. Thereby, polar anisotropic permanent magnets installed in a sleeve are drawn to a magnetic body installed in a rear side fixed body. An impeller is backwardly drawn against load caused by the blood pressure difference and applied toward a forward direction. Therefore, a front end surface of the sleeve does not approach a rear end surface of the front end fixed body very closely so that a micro gap can be certainly obtained.

The blood pressure difference produces load from a rear side to a front side and the load is applied toward a rotating impeller so as to move the front end surface of the sleeve to the rear end surface of the front fixed body. If the front end surface of the sleeve moves toward the rear end surface of the front fixed body very closely, the micro gap cannot be obtained sufficiently. The blood as a lubricant fluid cannot be flown smoothly. Further, the mechanical loss and damage become serious and an amount of dissolved blood is increased in the case that the micro gap cannot be maintained sufficiently. In order to avoid the above problems, a first magnet confronting with the rear end surface of the front end fixed body is installed in the sleeve and a second magnet confronting with the front end surface of the sleeve is installed in the front fixed body, wherein the same poles of the first magnet and the second magnet confront each other so as to produce a repulsive force therebetween. The first magnet is installed in the sleeve and the second magnet is installed in the front fixed body. Thus the sleeve and the front fixed body are repulsed from each other. That is, the impeller is repulsed forwardly against load caused by the blood pressure difference and shifted to the front side thereof so that the front end surface of the sleeve is prevented from approaching the rear end surface of the front fixed body very closely and a micro gap can be certainly provided.

The above magnets are preferably permanent magnets. The permanent magnets can maintain magnetic performance permanently so that a maintenance operation thereof can be omitted. The above magnets are preferably ring-shaped magnets arranged to be coaxial with a rotational axis of the impeller, respectively. Thereby, the impeller can be rotated smoothly and the mechanical loss and damages can be reduced.

As described above, in accordance with the present invention, an artificial cardiac pump comprises a housing, an impeller rotatably supported with respect to an axial body fixed in the housing and a driving mechanism for rotating the impeller, wherein blood is taken in from the front side of the impeller and force-fed to the rear side of the impeller along an axial direction by the impeller rotated by the driving mechanism, wherein the axial body connected and sandwiched between a front side fixed body and a rear side fixed body, wherein the front side fixed body is fixed at a straightening board protruded from an inner wall of the housing at a front side with respect to the impeller and the rear side fixed body is fixed at a board-shaped diffuser protruded from the inner wall of the housing at the rear side with respect to the impeller, the impeller comprising an inner peripheral surface confronting with an outer peripheral surface of the axial body with a micro gap, a sleeve of which the both end surfaces confronting with a rear end surface of the front side fixed body and a front end surface of the rear side fixed body with a micro gap, respectively and impeller wing-components protruded from an outer peripheral surface of the sleeve, and the driving mechanism comprising polar anisotropic permanent magnets installed in the sleeve and rotary magnetic flux generator installed in the housing and surrounding with a peripheral portion of the impeller. By rotating the impeller, blood is sucked into the housing from the front side of the impeller and the whirling component of the blood is controlled by passing though a straightening plate. Then, the blood is pressurized by passing through the impeller and introduced into a diffuser. In the diffuser, a hydrodynamic status is recovered to a static status while the blood is discharge to the rear side of the impeller. The part of the high-pressurized blood behind the impeller is introduced into a micro gap between the front end surface of the rear side fixed body and the rear end surface of the sleeve. As the result, the blood is introduced into a micro gap between the rear end surface of the front end fixed body and the front end surface of the sleeve though a micro gap between an outer peripheral surface of the axial body and an inner peripheral surface of the sleeve and then joined with blood in the housing. While the impeller is rotating, blood as a lubricant fluid is flown to the micro gaps between the sleeve and the rear end fixed body, the rear end fixed body and an axial body and the axial body and a front end fixed body in order. At the rotating impeller, radial load with respect to the impeller is supported by the axial body and thrust load with respect to the impeller is supported by the rear side fixed body and the front side fixed body in a non-contact relation.

In order to rotate the impeller, the polar anisotropic permanent magnets confronting with the rotary magnetic flux generator are installed in the sleeve as one of components of the impeller. Therefore, the artificial cardiac pump according to the present invention need not have a shroud utilized in a conventional artificial cardiac pump. Even if an unbalanced weight condition occurs at the sleeve located at the innermost portion of the impeller along the radius direction, baneful influence caused by hydrodynamic unbalance can be saved with respect to the impeller itself and its vibration can be also saved. Further, a length of an outer radius of the impeller can be shortened so that mechanical loss and damages can be controlled. In addition, the reverse flow of blood to a shroud that has often happened in a conventional artificial cardiac pump is completely resolved so that an efficiency of the pump according to the present invention can be improved.

Thrust hydrodynamic generation grooves for supporting thrust load applied to the impeller are provided at the rear end surface of the front side fixed body and the front end surface of the rear side fixed body which confront each end surface of the sleeve. While the impeller is rotating, thrust hydrodynamic is produced at the micro gap formed by the sleeve, the front side fixed body and the rear side fixed body in blood as a lubricant fluid. Thus, the blood can be flown stably and the thrust load applied on the impeller is effectively supported.

In the case that a ring-shaped magnetic body for confronting with an end surface of the sleeve is installed in the rear side fixed body, the polar anisotropic permanent magnets installed in the sleeve are drawn toward the magnetic body installed in the rear side fixed body. That is, the impeller itself is drawn backwardly against a load forwardly applied caused by a blood pressure difference. Under this condition, the front end surface of the sleeve does not approach the front end surface of the rear side fixed body too closely so that it can be possible to provide a micro gap in which blood as a lubricant fluid is flown smoothly.

Further, the first magnet for confronting with the rear end surface of the rear side fixed body is installed in the sleeve. The second magnet for confronting with the front end surface of the sleeve is installed in the front side fixed body. The first magnet and the second magnet are installed so as to confront with the same pole of the first and second magnets and a repulsion force is produced between the first magnet and the second magnet. Thus, the sleeve in which the first magnet is installed and the front side fixed body in which the second magnet is installed are repulsed from each other. Under this condition, the front end surface of the sleeve does not approach to the front end surface of the rear side fixed body too closely so that it can be possible to provide a micro gap in which blood as a lubricant fluid is flown smoothly.

In the case that the magnet is a permanent magnet, any maintenance for maintaining specific functions of the magnet is unnecessary. If the magnet has a ring-shape and is arranged coaxially with a rotational axis of the impeller, the impeller can be rotated smoothly and mechanical loss and damaged can be prevented.

DETAILED DESCRIPTION OF PREFERRED EMBODIMENTS

In order to reduce mechanical loss and damages in an artificial cardiac pump with an axial pump and to improve efficiency thereof, the present inventors have repeated structural experiments wherein an impeller is rotated in a housing in a non-contact relation. As a result, the present inventors paid attention to a shape of an impeller and then invented the present invention. A main feature of the artificial cardiac pump according to the present invention is to omit a shroud that must be required in a conventional improved artificial cardiac pump.

First Embodiment

Figure 1:
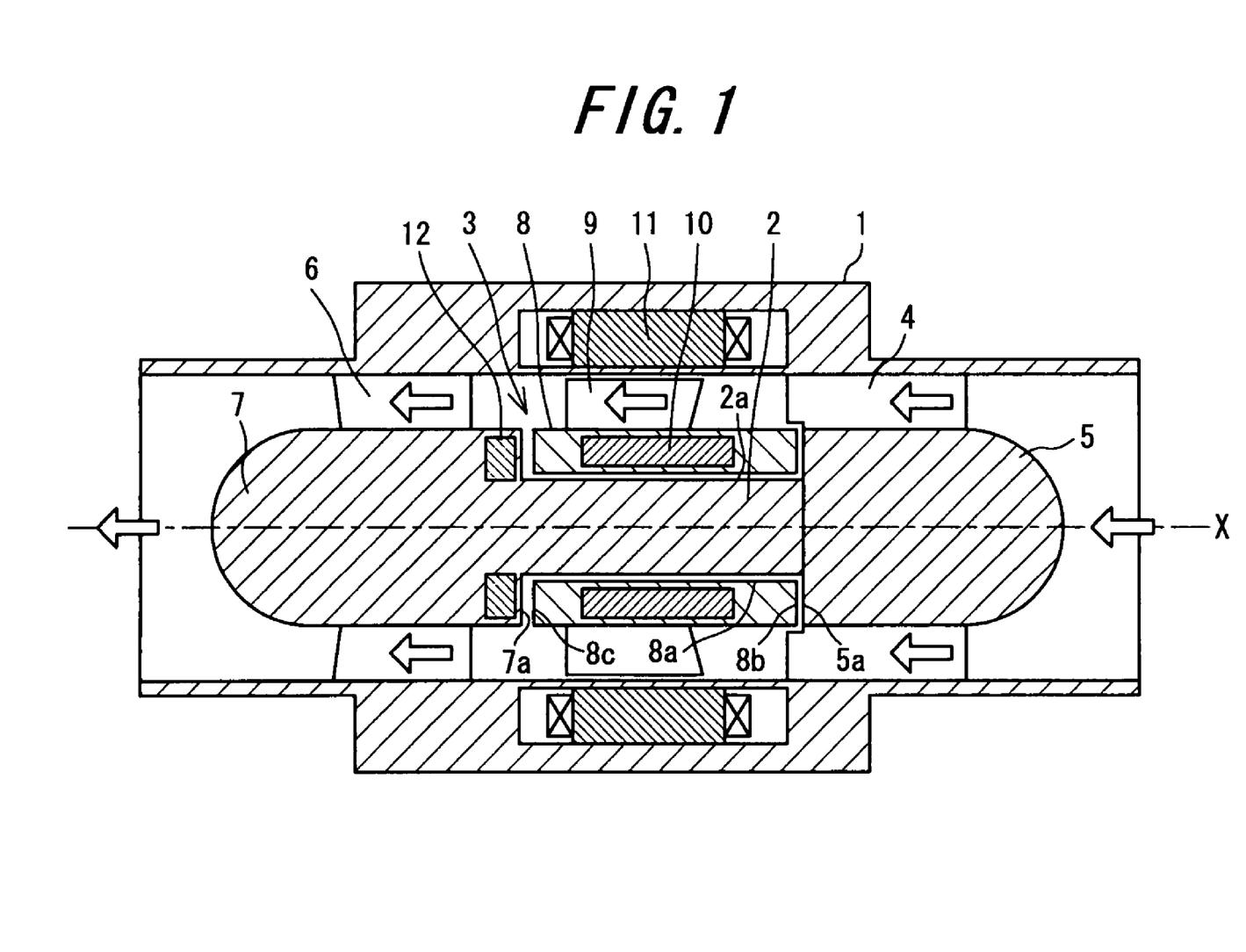
FIG. 1 shows a cross sectional view of one embodiment of an artificial cardiac pump according to the present invention.
Figure 2:
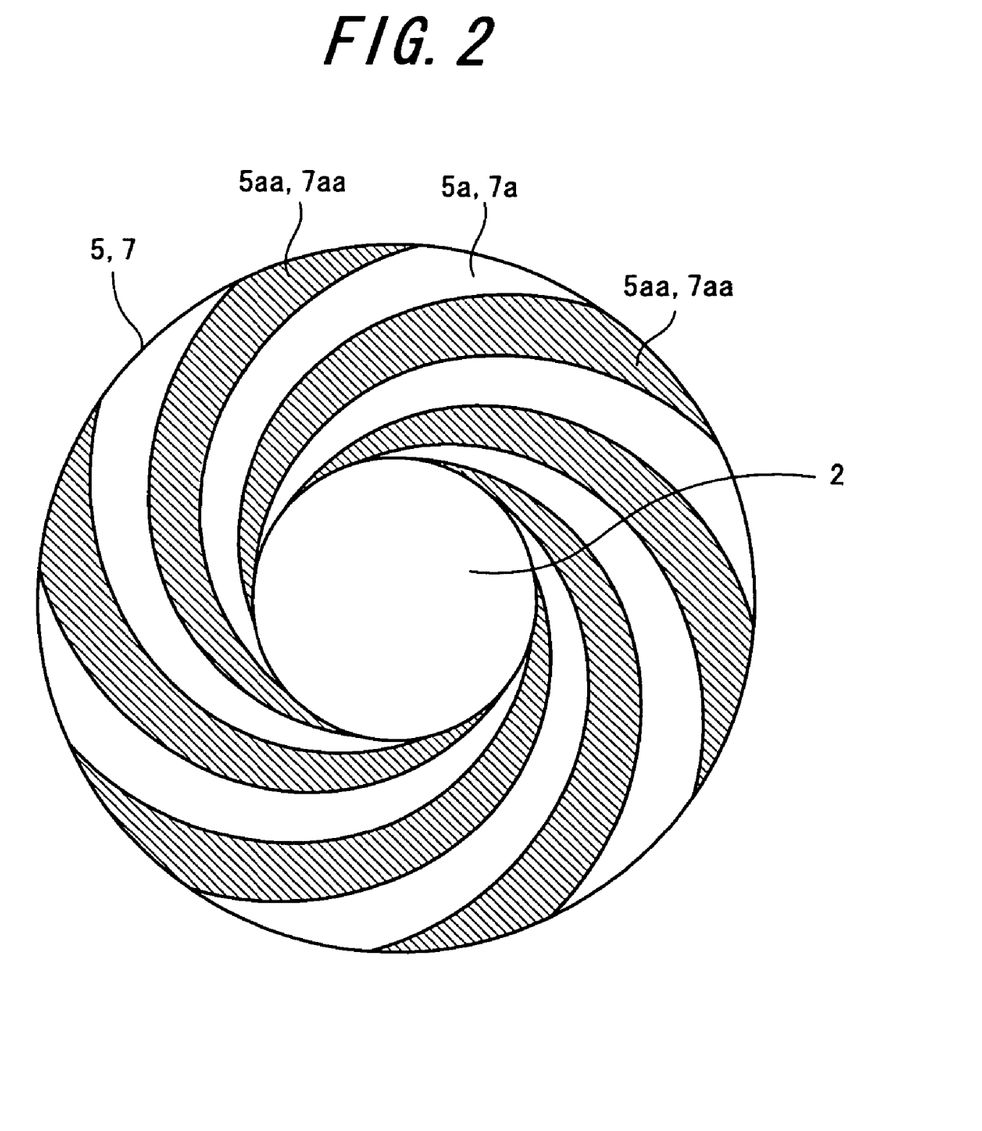
FIG. 2 shows a plane view of a rear end surface of a front side fixed body and a front end surface of a rear side fixed body for showing thrust hydrodynamic generation grooves in one embodiment of an artificial cardiac pump according to the present invention.

An embodiment of an artificial cardiac pump according to the present invention will be described with reference to the accompanying drawings. FIG. 1 shows a vertical cross sectional view of an embodiment of an artificial cardiac pump according to the present invention. FIG. 2 shows a plan view of a rear end surface of a front side fixed body and a front end surface of a rear side fixed body for showing thrust hydrodynamic grooves in its artificial cardiac pump. In the drawings, the same named components indicates the same numerals, respectively. Therefore, the description thereof is omitted.

As shown in FIG. 1, the embodiment of the artificial cardiac pump according to the present invention mainly comprises a cylindrical housing 1, a fixed axial body 2 as a central axis X in the housing, a rotor 3 that is an impeller rotatively supported in the housing with respect to the axial body 2 and a driving mechanism for rotating the rotor 3. By rotating the rotor 3, blood is taken from a front portion of the rotor 3 (right side in FIG. 1) and pressurized. Then, the blood is force-fed to a back portion of the rotor 3 (left side in FIG. 1) along an axial direction. In FIG. 1, a main blood route is indicated as white arrows.

Next, a detailed structure will be described. On an inner wall of the housing 1 located in front of the rotor 3, a plurality of straightening plate components are protruded and bonded as a straightening board 4. At an inner side of the straightening board 4, a cylindrical front side fixed body 5 is coaxially arranged with respect to the central axis X and bonded. On the other hand, on an inner wall of the housing 1 behind the rotor 3, a plurality of board-shaped diffuser components are protruded and bonded as a diffuser 6. At an inner side of the diffuser 6, a cylindrical rear side fixed body 7 is coaxially arranged and bonded. A rear end surface 5a of the front side fixed body 5 and a front end surface 7a of the rear side fixed body 7 are connected to the axial body 2. The axial body 2 can be fixed in the housing 1. Therein, each central portion of a front end of the front side fixed body 5 and a rear end of the rear side fixed body 7 is protruded, respectively. The former protruded portion introduces sucked blood to distribute the straightening board 4 without any resistance. The latter protruded portion introduces blood flown from the diffuser 6 so as to join the other blood without resistance.

On the axial body 2, a sleeve 8 is circularly fitted, wherein the sleeve 8 includes an inner peripheral surface 8a confronting with an outer peripheral surface 2a of the axial body 2 with a micro gap, a front end surface 8b confronting with the rear end surface 5a of the front side fixed body 5 with a micro gap and a rear end surface 8c confronting with the front end surface 7a of the rear side fixed body 7 with a micro gap. While the sleeve 8 is supported, the sleeve 8 is rotated with respect to the axial body 2 and movable between the rear end surface 5a of the front side fixed body 5 and the front end surface 7a of the rear side fixed body 7. Further, on an outer peripheral surface of the sleeve 8, a plurality of impeller wing-components 9 are protruded and bonded. The outer edge of the impeller is located close to an inner wall of the housing 1. The rotor 3 comprises the sleeve 8 and the impeller 9.

Polar anisotropic permanent magnets 10 are radially arranged with respect to the central axis X and installed in the sleeve 8. The polar anisotropic permanent magnets 10 produce magnet flux perpendicular to the outer peripheral surface of the sleeve 8. On the other hand, a motor stator 11 formed by an electromagnetic coil for producing magnetic flux perpendicular to the outer peripheral surface of the sleeve 8 surrounds an outer peripheral portion of the sleeve 8 and is installed in the housing 1. A driving mechanism for rotating the rotor 3 is formed by the polar anisotropic permanent magnets 10 and the motor stator 11.

According to the artificial cardiac pump as described above, while an electric current having different phases such as a three phase electric current is applied to the electromagnetic coil 3 of the motor stator 11, a driving force (rotational force) for rotating the polar anisotropic permanent magnets 10 is produced so that the sleeve 8 and the impellers 9 of the rotor 3 are integrally rotated with respect to the fixed axial body 2 of the housing 1. Thereby, blood sucked from the front side is taken into the housing 1 and the blood is flown through the straightening plate 4 so as to control whirling movement. The blood is pressurized by impeller 9 and introduced to the diffuser 6 so that a hydrodynamic status is recovered to a static status and the blood is discharged to the back side. Thus, as a fundamental function of an artificial cardiac pump, it is possible to force-feed blood under the pressure.

The pressure of the blood at the rear side (downstream) is higher than that at the front side (upstream) with respect to the impeller 9. A portion of high-pressurized blood behind the impeller 9 is introduced to a micro gap between the front end surface 7a of the rear fixed body 7 and the rear end surface 8c of the sleeve 8. Then, the blood is fed to a micro gap between the rear end surface 5a of the front side fixed body 5 and a front end surface 8b of the sleeve 8 through a micro gap between the outer peripheral surface 2a of the axial body 2 and the inner peripheral surface 8b of the sleeve 8. Accordingly, while the rotor 3 is rotating, blood as a lubricant fluid is flown to a gap between the sleeve 8 and the rear side fixed body 7, a gap between the rear side fixed body 7 and the axial body 2 and a gap between the axial body 2 and the front side fixed body 5 in order. At that time, the radial load applied to the rotor 3 is supported by the axial body 2 in a non-contact relation and the thrust load is supported by the rear side fixed body 7 and the front side fixed body 5 in a non-contact relation.

The blood pressure difference as described above provides a load onto the rotating rotor 3 from the rear side to the front side. As the result, the front end surface 8b of the sleeve 8 approaches the rear end surface 5a of the front side fixed body 5. If the front end surface 8b approaches the rear end surface 5a very closely, the micro gap between the front end surface 8b of the sleeve 8 and the rear end surface 5a of the front side fixed body 5 cannot be maintained sufficiently, and the blood as a lubricant fluid cannot be flown smoothly. Thus, mechanical loss and damages are increased and an amount of dissolved blood is increased.

Thus, in the embodiment according to the present invention, a ring-shaped magnet 12 (such as iron plate and iron mass) arranged at a location for confronting with the rear end surface 8c of the sleeve 8 is installed in the rear side fixed body 7. Thereby, the polar anisotropic permanent magnets 10 installed in the sleeve 8 are drawn toward the magnetic body 12 installed in the rear side fixed body 7. Accordingly, the rotor 3 is drawn backwardly against the load applied in the front direction caused by the blood pressure difference. Therefore, the front end surface 8b of the sleeve 8 is prevented from approaching the rear end surface 5a of the front side fixed body 5 very closely. A micro gap, in which blood as a lubricant fluid is flown stably and smoothly, can therefore be maintained with certainty.

Further, the load forwardly applied caused by the blood pressure difference or load suddenly varied along the central axis X in the case that the artificial cardiac pump is energized and driven is applied as a thrust load on the road. It may be baneful influenced to maintain the micro gap between the front end surface 8b of the sleeve 8 and the rear end surface 5a of the front side fixed body 5 and/or the micro gap between the rear end surface 8c of the sleeve 8 and the front end surface 7a of the rear end fixed body 7.

As shown in FIG. 2, in the embodiment, a plurality of spiral shaped front thrust hydrodynamic generation grooves 5aa (6 grooves are shown in FIG. 2) are provided at the rear end surface 5a of the front side fixed body 5. The front thrust hydrodynamic generation grooves 5aa apply thrust hydrodynamic to blood flown in a space between the grooves 5aa and the front end surface 8b of the sleeve 8. Thereby, the thrust load applied forwardly can be supported in the rotor 3.

Likewise, a plurality of spiral rear side thrust hydrodynamic generation grooves 7aa are formed on the front end surface 7a of the rear side fixed body 7. The rear side thrust hydrodynamic grooves 7aa apply thrust hydrodynamic to blood flown in a space between the rear side fixed body 7 and the rear end surface 8c. Thereby, the thrust load applied backwardly can be supported in the rotor 3. Particularly, the thrust hydrodynamic is affected in the case of the magnetic body 12 installed in the rear side fixed body 7. Such an effect is accomplished immediately after an excitation of the artificial cardiac pump. When the rotor 3 is stopped, a drawing force between the polar anisotropic permanent magnets 10 and the magnetic body 12 is only produced in the rotor 3. At the time, a contact relation between the rear end surface 8c of the sleeve 8 and the front end surface 7a of the rear side fixed body 7 is maintained. At the beginning, when the rotor is energized from this condition, the thrust hydrodynamic is immediately produced by blood taken into a gap between the rear end surface 8c of the sleeve 8 and the front end surface 7a of the rear side fixed body 7 so as to shift in a non-contact relation.

Accordingly, when the rotor 3 is rotating, the thrust hydrodynamic pressure occurs at micro spaces formed by the sleeve 8, the front end fixed body 5 and the rear side fixed body 7 through blood as a lubricant fluid. Thus, the blood can flow stably by accurately providing these micro gaps and the thrust load applied on the rotor 3 can be effectively supported.

As described above, in the artificial cardiac pump according to the present invention, the polar anisotropic permanent magnets 10 for confronting with the motor stator 11 are installed in the sleeve 8 as a component of the rotor in order to rotate the rotor 3. Therefore, it is unnecessary to provide a shroud 120 (see FIG. 3) utilized in a conventional improved artificial cardiac pump.

Accordingly, even if an unbalanced weight condition occurs at the sleeve 8 located at an inner most portion of the rotor with respect to a radius direction, baneful influence for a dynamic balance of the rotating rotor 3 is reduced and a degree of a vibration of the rotor 3 is reduced. Further, a length of an outer diameter of the rotor can be shortened and the mechanical loss and damages can be reduced. Further, situations in which blood is reversely flown to the shroud 120 as utilized in the conventional improved artificial cardiac pump completely disappear and the pump efficiency can be improved.

Upon comparing the conventional improved artificial cardiac pump with the pump according to the present invention, a relative distance between the polar anisotropic permanent magnets 10 and the motor stator 11 is relatively large in the present invention. Although the motor driving efficiency becomes slightly lower, the rotational force applied to the rotor 3 itself is not substantially influenced since an electric current level and a winding number of an electromagnetic coil are varied and the rotational force of the rotor 3 is controlled by coerecivity of the polar anisotropic permanent magnets 10.

Second Embodiment

Figure 4:
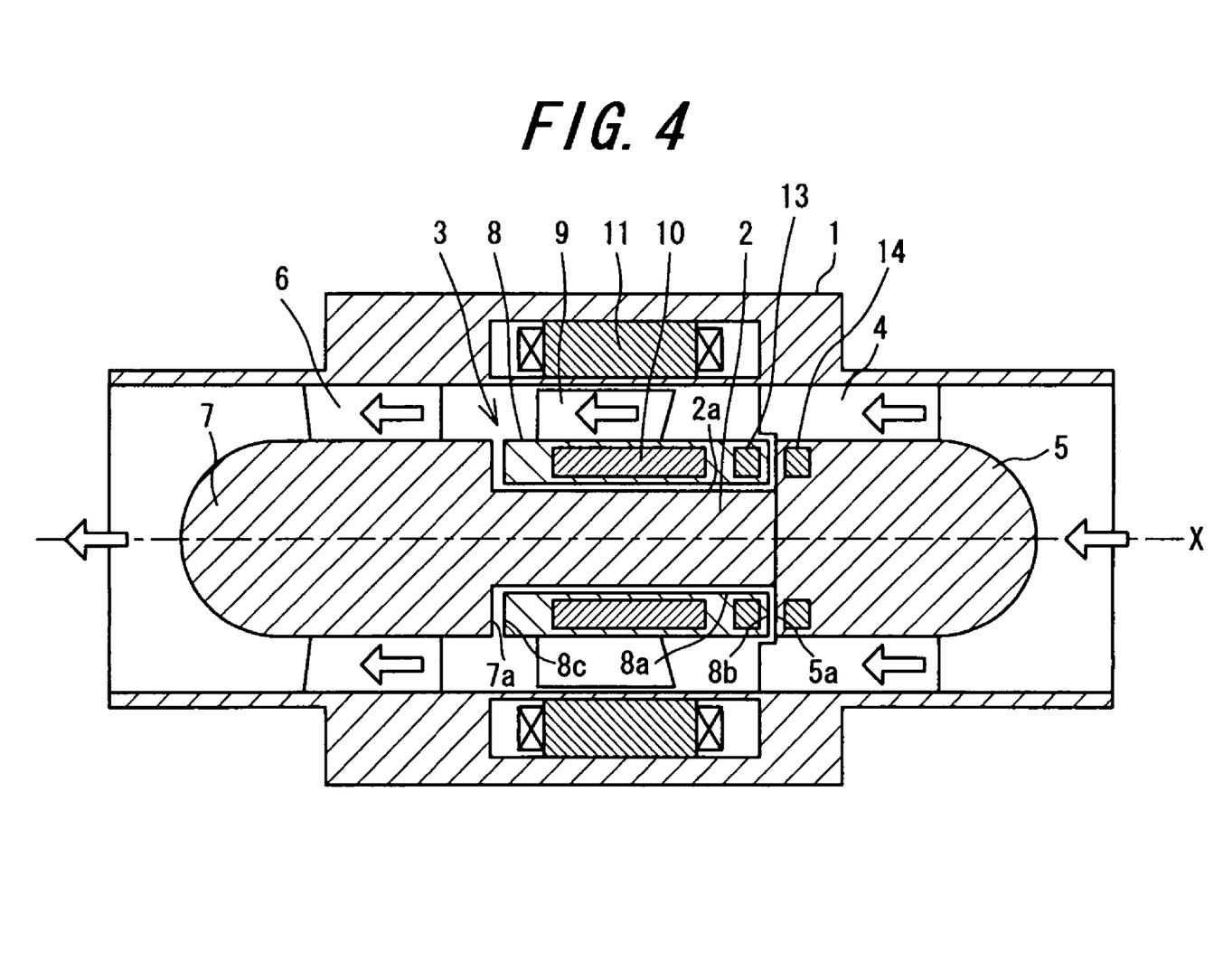
FIG. 4 shows a vertical cross sectional view of another embodiment of an artificial cardiac pump according to the present invention.

Next, the second embodiment of the artificial cardiac pump according to the present invention will be described with reference to the drawings. FIG. 4 shows a cross sectional view of a structure of the second embodiment of the artificial cardiac pump according to the present invention. The embodiment is one of the variations modified from the first embodiment as described above, wherein the same named components are numbered with the same reference numbers in the first embodiment of the artificial cardiac pump, respectively. The explanation thereof is omitted.

As shown in the drawings, the second embodiment of the artificial cardiac pump comprises a permanent magnet 13 as the first magnet and a permanent magnet 14 as the second magnet instead of the magnetic body 12. The permanent magnet 13 is installed in the sleeve at which the permanent magnet 13 is confronting with a rear end surface 5a of a front side fixed body 5. The permanent magnet 14 is installed in the front side fixed body 5 at which the permanent magnet 14 is confronting with a front end surface 8b of the sleeve 8. The permanent magnets 13 and 14 have a ring shape of which an axis is coaxial with a rotational axis of the rotor (impellers) 3.

Both of the permanent magnets 13 and 14 produce magnet flux parallel to the central axis X. The same poles thereof are confronting each other so as to produce a repulsion force between the permanent magnet 13 and the permanent magnet 14. Accordingly, the permanent magnets 13 and 14 have a function as a thrust bearing along an axial direction of the central axis X. The rotor 3 is repulsed backwardly against the load caused by the blood pressure difference which is applied in the forward direction. Therefore, the front end surface 8b of the sleeve 8 does not approach the rear end surface 5a of the front side fixed body 5 very closely, so that a micro gap can be accurately provided such that blood as a lubricant fluid can flow stably.

While the artificial cardiac pump is stopped or driven at a low speed, the attractive force between the motor stator 11 and the polar anisotropic permanent magnets 10 and the repulsion force between the permanent magnet 13 and the permanent magnet 14 are balanced. Thus, the rotor 3 is moved downwardly so as to prevent the rear end surface 8c of the sleeve 8 from contacting with the front end surface 7a of the rear side fixed body 7.

Regarding the magnetic force of the permanent magnets 13 and 14, it is preferable to note load applied forward by rotating the rotor 3. Depending on rotational speed of the rotor 3, a value of a produced load is varied. Judging from a produced load corresponding to a rotational speed range of the rotor 3, the magnetic force is designed such that the front end surface 8b of the sleeve 8 does not contact the rear end surface 5a of the front side fixed body 5 even if the maximum load is produced. For example, even if the minimum load is produced, the front end surface 8c of the sleeve is designed not to contact the front end surface 7a of the rear side fixed body 7. In the case of adjusting the magnetic force, it may provide a magnetic body 12 employed in the first embodiment together with the permanent magnets 13 and 14 employed in the second embodiment.

The present invention is not restricted by any embodiments as described above. Various amendments may be acceptable unless a variation is within a scope of the present invention. For example, a cross sectional surface of the inner peripheral surface 8a of the sleeve 8 is preferably a complete circle. On the other hand, a cross sectional surface of the axial body 2 is preferably an offset combination formed by two half-circles or four quarter-circles wherein a plurality of arc portions are existed. In such a case, a micro gap between an outer peripheral surface 2a of the axial body 2 and an inner peripheral surface 8a of the sleeve 8 can be certainly provided so as to flow blood as lubricant fluid smoothly. A shape of the front side thrust hydrodynamic generation groove 5aa and a shape of the rear side thrust hydrodynamic generation groove 7aa is not only spiral but also radial.

UTILITY IN THE INDUSTRY

The present invention relates to an artificial cardiac pump and is useful as a substitute or an auxiliary of a heart of a living body.

What is claimed is:
1. An artificial cardiac pump comprising:
a housing;
an axial body fixed in said housing;
an impeller arranged so as to be rotatable around said axial body, said axial body extending through said impeller;
a driving mechanism for rotating said impeller such that blood taken in from a front side of said impeller is force-fed to a rear side of said impeller along an axial direction of said impeller;
a front-side fixed body connected to a front side of said axial body;
a rear-side fixed body connected to a rear side of said axial body such that said axial body is sandwiched between said front-side fixed body and said rear-side fixed body;
a straightening board protruding from an inner wall of said housing at the front side of said impeller, said front-side fixed body being fixed at said straightening board; and
a board-shaped diffuser protruding from said inner wall of said housing at the rear side of said impeller, said rear-side fixed body being fixed at said board-shaped diffuser,
wherein said impeller includes a sleeve and impeller wing-components protruding from an outer peripheral surface of said sleeve, said sleeve being arranged such that an inner peripheral surface of said sleeve faces an outer peripheral surface of said axial body across a gap, a front-end surface of said sleeve faces a rear-end surface of said front-side fixed body across a gap, and such that a rear-end surface of said sleeve faces a front-end surface of said rear-side fixed body across a gap,
wherein said driving mechanism comprises polar anisotropic permanent magnets installed in said sleeve and a rotary magnetic flux generator installed in said housing so as to surround an outer peripheral portion of said impeller, and
wherein said sleeve includes a first magnet arranged to face said rear-end surface of said front-side fixed body, and said front-side fixed body includes a second magnet arranged to face said front-end surface of said sleeve, said first and second magnets being permanent magnets, said first and second magnets being arranged such that a pole of said first magnet faces a same pole of said second magnet so as to produce a repulsion force in an axial direction of the axial body between said first magnet and said second magnet.
2. An artificial cardiac pump as claimed in claim 1, wherein thrust hydrodynamic generation grooves for supporting a thrust load applied to said impeller are provided at said rear-end surface of said front-side fixed body and at said front-end surface of said rear-side fixed body.

3. An artificial cardiac pump as claimed in claim 1, wherein said first magnet and said second magnet each have a ring-shape and are each arranged coaxially with a rotational axis of said impeller.

4. An artificial cardiac pump as claimed in claim 1, wherein said axial body extends through an entirety of said impeller.

5. An artificial cardiac pump as claimed in claim 1, wherein said sleeve is arranged such that said front-end surface of said sleeve opposes said rear-end surface of said front-side fixed body in the axial direction of said axial body.

6. An artificial cardiac pump as claimed in claim 1, wherein said first and second magnets are arranged such that said pole of said first magnet faces said same pole of said second magnet in the axial direction of said axial body.

* * * * *